United States Patent [19]

Nakahara et al.

[11] Patent Number: 5,733,984
[45] Date of Patent: Mar. 31, 1998

[54] PROCESS FOR THE PREPARATION OF A DEUTERATED COMPOUND

[75] Inventors: Masaru Nakahara, 6-1012, 3-ban, Chagasaki, Ohtsu-shi, Shiga; Heiji Enomoto, 5-16, Kagitori 4-chome, Taihaku-ku, Sendai-shi, Miyagi; Atsushi Kishita, Seikaen haitu-201-sitsu, 9-10, Seikaen 1-chome, Aoba-ku, Sendai-shi, Miyagi; Kenji Tsuda, Hiroshima; Toshinari Tennoh, Hiroshima; Emi Fujita, Hiroshima, all of Japan

[73] Assignees: Masaru Nakahara, Shiga; Heiji Enomoto; Atsushi Kishita, both of Miyagi; Nishikawa Rubber Co., Ltd., Hiroshima, all of Japan

[21] Appl. No.: 754,255

[22] Filed: Nov. 20, 1996

[30] Foreign Application Priority Data

Nov. 24, 1995 [JP] Japan .................................. 7-327868

[51] Int. Cl.⁶ .................................................. C08F 8/00
[52] U.S. Cl. ................. 525/383; 525/332.8; 525/332.9; 525/333.1; 525/333.2; 536/22.1; 585/899; 423/647.7
[58] Field of Search .......................... 525/383; 536/22.1; 585/899; 423/647.7

[56] References Cited

U.S. PATENT DOCUMENTS

| | | | |
|---|---|---|---|
| 4,134,843 | 1/1979 | Rebuck et al. | 252/28 |
| 4,421,865 | 12/1983 | Shen | 568/902 |
| 5,149,820 | 9/1992 | Borretzen et al. | 548/215 |
| 5,221,768 | 6/1993 | Kato et al. | 562/598 |

FOREIGN PATENT DOCUMENTS

| | | |
|---|---|---|
| 59-105079 | 6/1984 | Japan . |
| 63-27443 | 2/1988 | Japan . |

*Primary Examiner*—Bernard Lipman
*Attorney, Agent, or Firm*—Sughrue, Mion, Zinn, Macpeak & Seas, PLLC

[57] ABSTRACT

A process for the preparation of a deuterated compound, which requires neither many steps nor an expensive reagent, and is considerably economical and can be widely used for general-purposes because raw materials which can be used therein are not particularly limited. Specifically, a deuterated compound is obtained by a process comprising treating an organic compound (an aliphatic or alicyclic compound, an aromatic hydrocarbon or a polymer compound such as rubbers and proteins) in heavy water under high-temperature and high-pressure conditions not less than the subcritical temperature and the subcritical pressure.

6 Claims, No Drawings

PROCESS FOR THE PREPARATION OF A DEUTERATED COMPOUND

FIELD OF THE INVENTION

The present invention relates to a process for the preparation of a deuterated compound which is useful as a raw material for pharmaceuticals, agricultural chemicals, functional materials, analytical tracers and the like.

BACKGROUND OF THE INVENTION

The preparation of a deuterated compound has conventionally required a large number of steps, which inevitably raises the cost of the deuterated compound remarkably (tens of thousands yen per g for common imported products). In addition, there is a limitation to the kind of available deuterated compounds.

SUMMARY OF THE INVENTION

An object of the present invention is therefore to solve the above-described problems, thereby providing a process for preparing a deuterated compound, which requires neither a number of steps nor an expensive reagent, and thus is considerably economical and can be widely used for general-purposes.

Other objects and effects of the present invention will be apparent from the following description.

The present inventors conducted extensive investigations for achieving the above objects. As a result, it has been found that the above objects can be attained by treating an organic compound in heavy water under a high-temperature and high-pressure condition wherein the high temperature and the high pressure are, respectively, not less than the subcritical temperature and the subcritical pressure, preferably not less than the critical temperature and the critical pressure, thus leading to the present invention.

DETAILED DESCRIPTION OF THE INVENTION

Any organic compounds can be used as a raw material for use in the present invention. Preferred examples of the organic compound include aliphatic compounds, alicyclic compounds, aromatic hydrocarbons, polymer compounds such as rubbers and proteins.

Specific examples of the aliphatic organic compound suitably used in the present invention include pentane, hexane, heptane, octane, methanol, ethanol, 2-propanol, ethyl acetate, diethyl ether, dichloromethane, dibromoethane, 2,2,2-trifluoroethanol, hexafluoroisopropanol, 1,1,2,2-tetrachloroethane and nitroethane.

Specific examples of the alicyclic compound include cyclohexane, methyl cyclohexane, pyridine and tetrahydrofuran.

Specific examples of the aromatic hydrocarbons include benzene, toluene, ethylbenzene, xylene, bromobenzene, chlorobenzene, dichlorobenzene, nitrobenzene, phenol, hydroquinone, benzoic acid, salicylic acid, phthalic acid and aniline.

Specific examples of the rubber usable in the present invention include natural rubber, isoprene rubber, butadiene rubber, 1,2-polybutadiene rubber, styrene-butadiene rubber, chloroprene rubber, nitrile rubber, butyl rubber, ethylene propylene rubber, chlorosulfonated polyethylene, acrylic rubber, epichlorohydrin rubber, polysulfide rubber, fluororubber and urethane rubber.

Heavy water is deuterium oxide ($D_2O$) which contains an isotope of hydrogen different from that contained in so-called water ($H_2O$). It is generally prepared by adding sodium hydroxide to water as an electrolyte followed by fractional electrolysis, or by making use of deuteration. Heavy water for use in the present invention must be under a high-temperature and high-pressure condition where the temperature and the pressure are, respectively, not less than its subcritical temperature and pressure, preferably not less than its critical temperature and pressure (supercritical conditions), during the deuterating process.

Heavy water under a high-temperature and high pressure condition including the above described supercritical condition is described in detail below.

It is generally considered that the critical condition of a whole reaction system differ with that of a substance used in the chemical reaction. The critical condition in a mixed system have not been theoretically elucidated. However, in the present invention, both of the temperature and pressure can be uniform in the chemical reaction system (hermetically-sealed system) used therein irrespective of the kind of an organic compound used for the chemical reaction. Accordingly, it can be understood that heavy water in the reaction system is under the critical condition or higher so long as the temperature and the pressure in the reaction system are not less than 371° C. and 21.7 MPa, respectively, which are the critical condition of heavy water.

Specifically, the high-temperature and high-pressure condition for use in the present invention is not less than the subcritical condition generally having a temperature of from 200° to 371° C. and a pressure of from 5 to 21.7 Mpa, and preferably not less than the critical condition having a temperature of at least 371° C., more preferably from 371° to 500° C., and a pressure of at least 21.7 MPa, more preferably from 21.7 to 50 Mpa.

The present invention will be described in detail with reference to the following Examples, but the invention should not be construed as being limited thereto.

EXAMPLE 1

In a pressure vessel having an internal volume of 42 ml, 9 ml of heavy water containing 1N NaOH and 4 g of a vulcanized rubber (composed of an ethylene-propylene-diene terpolymer base synthetic rubber (EPDM polymer)) were placed, followed by allowing to react at 420° C. for 30 minutes in a heating oven. The reaction mixture was air-cooled sufficiently and then filtered to obtain an oily substance. The oily substance was analyzed using a nuclear magnetic resonance (NMR) spectroscopy. The results were as follows: $NMR^2H$-spectrum δ ppm (neat) relative to TMS:

0.9 (hydrogen constituting methyl), 1.25 (hydrogen constituting methylene), 1.6 (hydrogen constituting methine), 2.0; and D-conversion rate (D/H ratio): 0.03 (δ0.9), 0.01 (δ1.25), 3.9(δ1.6), 1.3 (δ2.0).

Under the same detection condition as in the above described NMR spectroscopic measurement, a signal of a naturally existing D ratio (represented by an order of mM) was not detected.

EXAMPLE 2

In a pressure vessel having an internal volume of 42 ml, 10 ml of heavy water containing 1N NaOH and 1 g of benzene were placed, followed by allowing to react at 350° C., 400° C. and 450° C., respectively, for 10 minutes in a heating oven. The products were analyzed by NMR in the same manner as in Example 1. The relation between the deuteration ratio Of hydrogen in benzene (D-conversion rate) and the reaction temperature obtained is shown in Table 1.

TABLE 1

| Reaction temperature (°C.) | D-conversion rate (%) |
|---|---|
| 350 | 50 |
| 400 | 80 |
| 450 | 90 |

As described above, an organic compound is treated in heavy water under high-temperature and high-pressure conditions including those exceeding the critical temperature and critical pressure according to the process of the present invention. The process for the preparation of a deuterated compound requires neither many steps nor an expensive reagent. Moreover, raw materials which can be used in the process of the invention are not particularly limited. Accordingly, the invention provides a preparation process of a deuterated compound, which is considerably economical and can be widely used for general-purposes.

While the invention has been described in detail and with reference to specific Examples thereof, it will be apparent to one skilled in the art that various changes and modifications can be made therein without departing from the spirit and scope thereof.

What is claimed is:

1. A process for the preparation of a deuterated compound which comprises treating an organic compound in heavy water under a high-temperature and high-pressure condition wherein said high temperature and said high pressure are not less than the subcritical temperature and the subcritical pressure, respectively.

2. The process according to claim 1, wherein said high-temperature and said high-pressure are not less than the critical temperature and the critical pressure, respectively.

3. The process according to claim 1, wherein said organic compound is an aliphatic or alicyclic compound or an aromatic hydrocarbon.

4. The process according to claim 2, wherein said organic compound is an aliphatic or alicyclic compound or an aromatic hydrocarbon.

5. The process according to claim 1, wherein the organic compound is a polymer compound selected from the group consisting of rubbers and proteins.

6. The process according to claim 2, wherein the organic compound is a polymer compound selected from the group consisting of rubbers and proteins.

* * * * *